(12) United States Patent
Okamoto

(10) Patent No.: US 10,413,163 B2
(45) Date of Patent: Sep. 17, 2019

(54) INTRODUCTION DEVICE AND ENDOSCOPIC APPARATUS

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/940,688

(22) Filed: Nov. 13, 2015

(65) Prior Publication Data

US 2016/0066771 A1 Mar. 10, 2016

Related U.S. Application Data

(63) Continuation of application No. PCT/JP2014/061012, filed on Apr. 18, 2014.

(30) Foreign Application Priority Data

Jun. 18, 2013 (JP) .................................. 2013-127350

(51) Int. Cl.
*A61B 1/00* (2006.01)
*A61B 1/005* (2006.01)
*G02B 23/24* (2006.01)

(52) U.S. Cl.
CPC ........ *A61B 1/0053* (2013.01); *A61B 1/00039* (2013.01); *A61B 1/0052* (2013.01);
(Continued)

(58) Field of Classification Search
CPC ............................ A61B 1/0053; A61B 1/0052
(Continued)

(56) References Cited

U.S. PATENT DOCUMENTS

2012/0302829 A1* 11/2012 Omoto ................. A61B 1/0052
600/109
2013/0190566 A1* 7/2013 Miyoshi ............... A61B 1/0057
600/131
2014/0135580 A1* 5/2014 Omoto ................. A61B 1/0052
600/148

FOREIGN PATENT DOCUMENTS

WO WO 2012/063880 * 5/2012
WO WO 2012/063880 A1 5/2012
WO WO 2012/074013 A1 6/2012

OTHER PUBLICATIONS

International Search Report dated Jul. 22, 2014 issued in PCT/JP2014/061012.

(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An introduction device includes, a grip portion which has a first wall portion, and a second wall portion, a curving portion which is configured to curve in a first surface and in a second surface that intersects at right angles with the first surface, a first dial portion which is rotatably provided in the first wall portion and which curves the curving portion in the first surface in accordance with a rotation amount, and a dial unit includes a shaft rotatably provided on the second wall portion, and a second dial portion which is fixed to the shaft and which curves the curving portion in the second surface in accordance with a rotation amount, the shaft being oblique to the longitudinal axis when seen from the side of the second wall portion.

7 Claims, 12 Drawing Sheets

(52) U.S. Cl.
CPC ........ *A61B 1/0055* (2013.01); *A61B 1/00066* (2013.01); *G02B 23/2476* (2013.01)

(58) Field of Classification Search
USPC ................................................. 600/146, 131
See application file for complete search history.

(56) References Cited

OTHER PUBLICATIONS

Japanese Office Action dated Apr. 7, 2014 issued in JP 2015-504793.
English translation of International Preliminary Report on Patentability dated Dec. 30, 2015 together with the Written Opinion received in related International Application No. PCT/JP2014/061012.
Chinese Office Action dated Dec. 1, 2016 in related Chinese Patent Application No. 201480035043.1.

\* cited by examiner

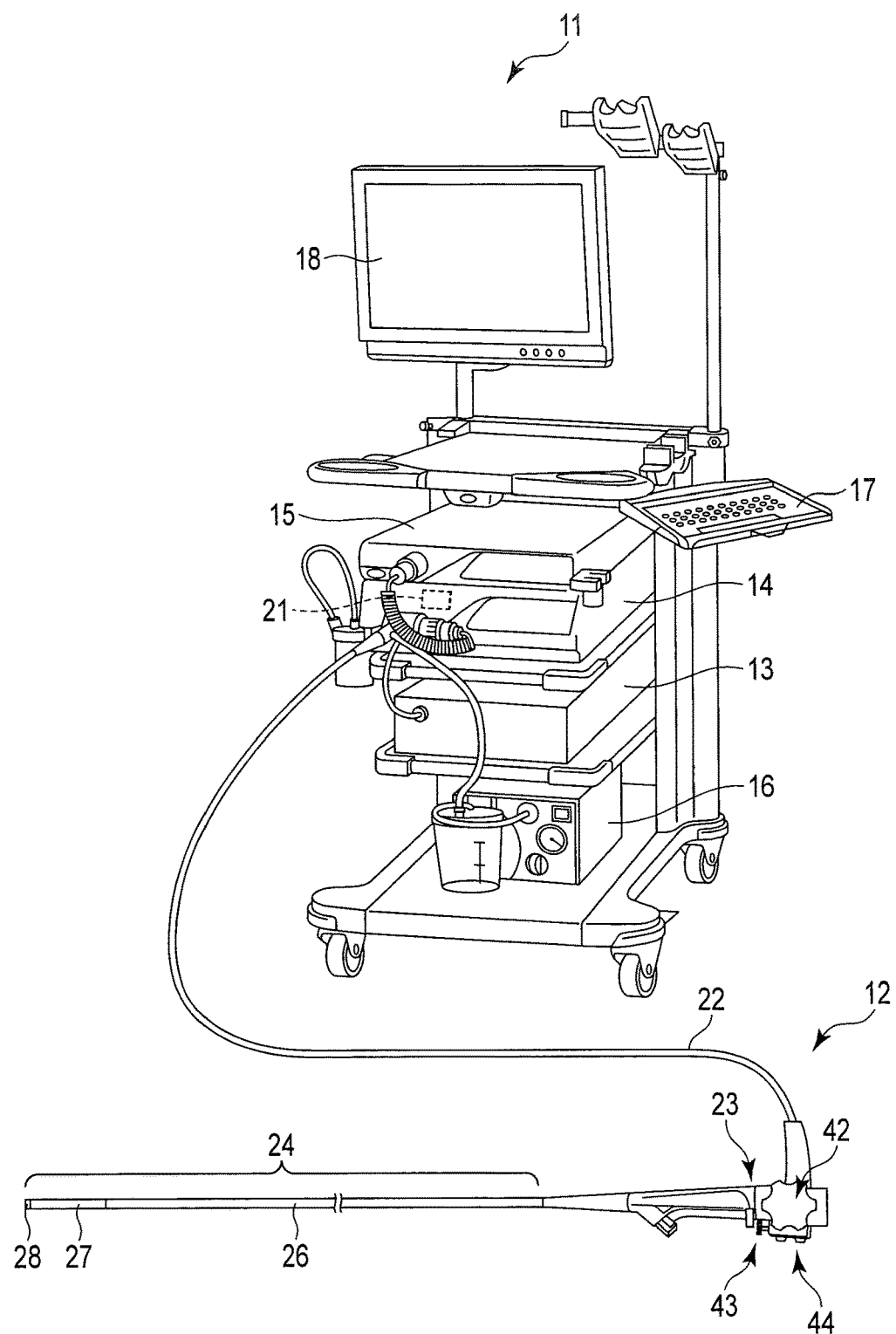
F I G. 1

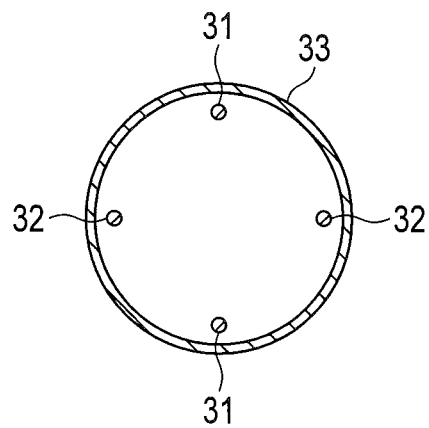
F I G. 4
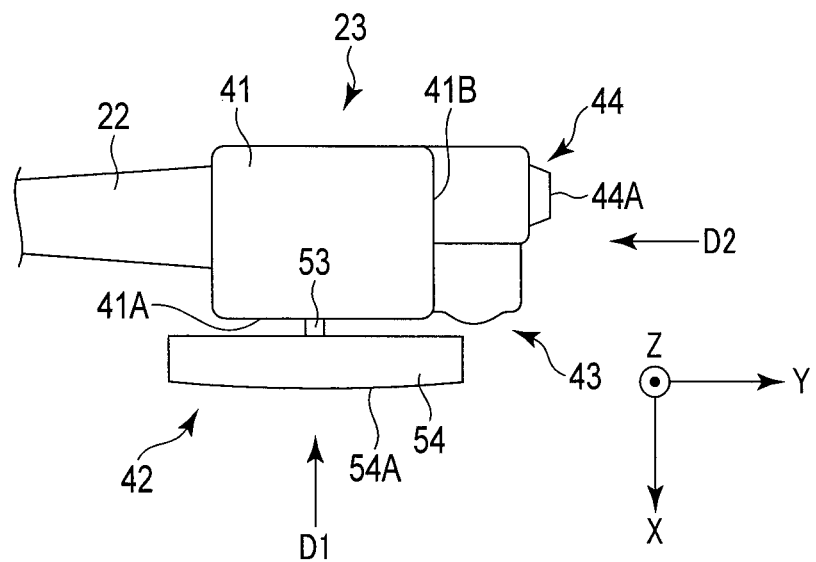
F I G. 5

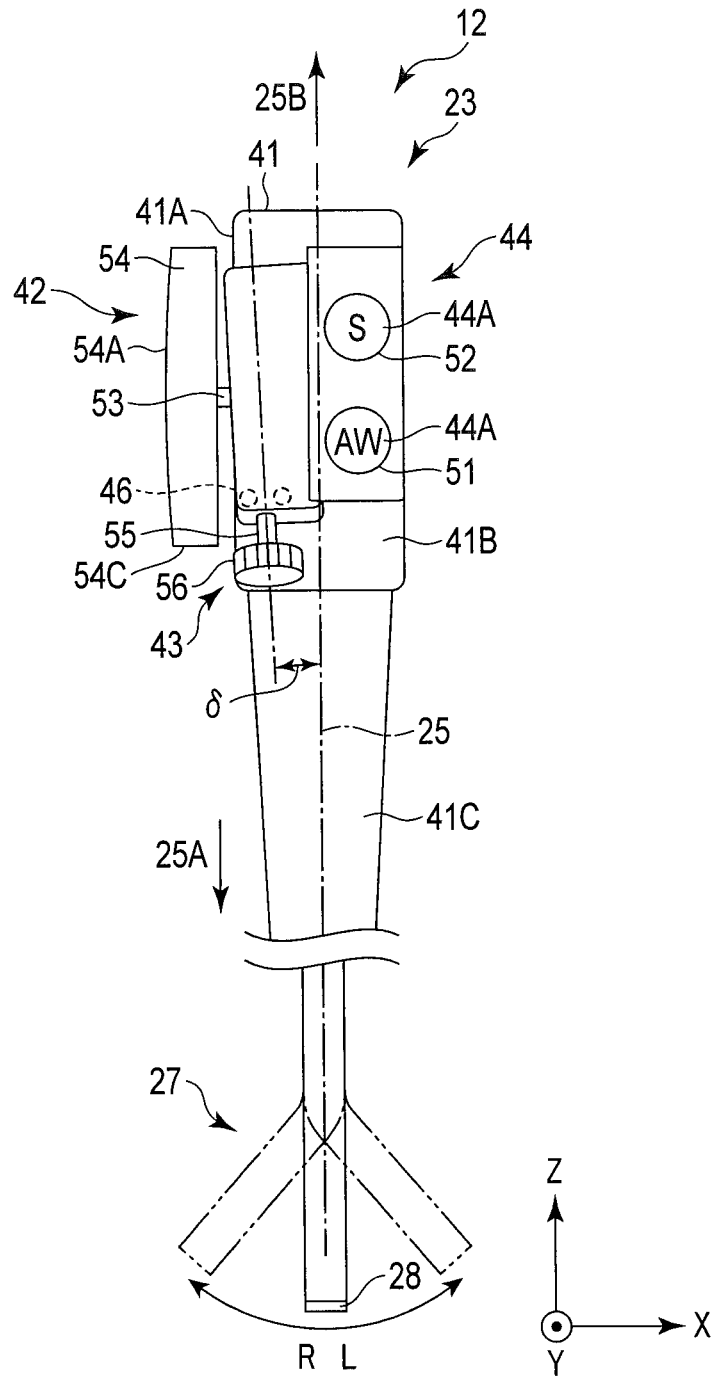
F I G. 11

INTRODUCTION DEVICE AND ENDOSCOPIC APPARATUS

CROSS-REFERENCE TO RELATED APPLICATIONS

This application is a Continuation Application of PCT Application No. PCT/JP2014/061012, filed Apr. 18, 2014 and based upon and claiming the benefit of priority from Japanese Patent Application No. 2013-127350, filed Jun. 18, 2013, the entire contents of which are incorporated herein by reference.

TECHNICAL FIELD

The present invention relates to an introduction device to be inserted into a sample, and an endoscopic apparatus capable of observing the inside of the sample.

BACKGROUND ART

In general, an endoscope has a flexible insertion portion to be inserted into a sample to, for example, observe and treat a lesion in the sample, and an operation portion to perform operations to curve the insertion portion in four directions (U-direction, D-direction, R-direction, and L-direction). The operation portion has a UD angle knob to perform the operations in the U-direction and the D-direction, and an RL angle knob to perform the operations in the R-direction and the L-direction. When the lesion is, for example, observed and treated, the UD angle knob and the RL angle knob are properly operated so that the insertion portion can be curved in the U-direction, the D-direction, the R-direction, and the L-direction.

There is another endoscope which drives a motor to rotate a curving portion in the U-direction, the D-direction, the R-direction, and the L-direction.

For example, an endoscope according to International Publication No. 2012/074013 enables a manual operation to be performed to curve a curving portion of an insertion portion in the upward (U) direction and the downward (D) direction, and enables an automatic operation to be performed by the driving of a motor to curve the curving portion in the leftward (L) direction and the rightward (R) direction. An operation portion is provided with a knob to be operated to curve the curving portion in the upward (U) direction and the downward (D) direction, and a dial to be operated to curve the curving portion in the leftward (L) direction and the rightward (R) direction.

CITATION LIST

Patent Literature

Patent Literature 1: International Publication No. 2012/074013

SUMMARY OF INVENTION

In the meantime, the size of the hands of a doctor who is the user of an introduction device of, for example, an endoscope varies from person to person. For example, there is a difference of the average hand size between male doctors and female doctors, and the average hand size also differs depending on the races of doctors. Thus, there has been a demand for an introduction device in which user's operability is improved in the operation to curve the curving portion.

An object of the present invention is to provide an introduction device and an endoscopic apparatus in which operability for curving a curving portion is improved.

An introduction device comprises a grip portion which comprises a first wall portion, and a second wall portion extending in a direction that intersects at right angles with the first wall portion, a curving portion which is provided along a longitudinal axis of the grip portion and which is configured to curve in a first surface and in a second surface that intersects at right angles with the first surface, a first dial portion which is rotatably provided in the first wall portion and which curves the curving portion in the first surface in accordance with a rotation amount, and a dial unit comprising a shaft rotatably provided on the second wall portion, and a second dial portion which is fixed to the shaft and which curves the curving portion in the second surface in accordance with a rotation amount, the shaft being oblique to the longitudinal axis when seen from the side of the second wall portion.

BRIEF DESCRIPTION OF DRAWINGS

FIG. 1 is a perspective view showing the overall configuration of an endoscopic apparatus according to a first embodiment;

FIG. 4 is a sectional view taken along the line F4-F4 shown in FIG. 3;

FIG. 5 is a schematic diagram showing an operation portion of the endoscopic apparatus shown in FIG. 1 from a proximal direction opposite to a distal direction of the longitudinal axis;

FIG. 11 is a schematic diagram showing the operation portion of the endoscopic apparatus shown in FIG. 10 from the direction D2 in which the second wall portion is seen;

DESCRIPTION OF EMBODIMENTS

[First Embodiment]

Figure 2:
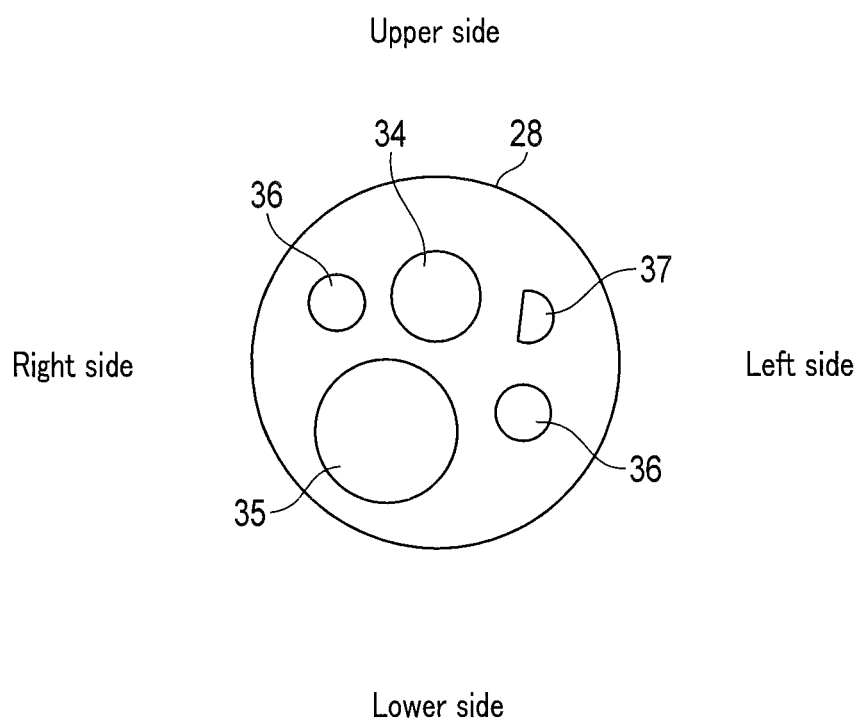
FIG. 2 is a front view showing the end face of the distal end of the endoscopic apparatus shown in FIG. 1.

FIG. 1 shows the overall configuration diagram of an endoscopic apparatus according to a first embodiment. As shown in FIG. 1, an endoscopic apparatus 11 has an endoscope 12, a control device 13, a light source device 14, an image taking device 15, an air/water/suction device 16, a keyboard 17, a monitor 18, and an actuator section 21.

The light source device 14 supplies light to an illumination lens 36 in a later-described distal hard portion 28 of the endoscope 12 under the control of the control device 13. The air/water/suction device 16 supplies air/water to a nozzle 37 in the distal hard portion 28 of the endoscope 12 or sucks liquid or tissues from a living body via the nozzle 37 under the control of the control device 13. The image taking device 15 performs image processing for an image of a subject photographed through an objective lens 34 of the distal hard portion 28 of the endoscope 12 to display the image on the monitor 18 under the control of the control device 13.

The control device 13 is connected to a rotation detection sensor 45 (see FIG. 6) incorporated in a later-described operation portion 23 of the endoscope 12. The endoscope 12 detects the rotation direction and the rotation amount of a second dial portion 56 by the rotation detection sensor 45, and transmits a detection signal to the control device 13. The control device 13 actuates the actuator section 21 in accordance with the rotation amount detected by the rotation detection sensor 45, and curves a curving portion 27 in the R-direction and the L-direction. The control device 13 is an example of a control section.

The actuator section 21 can provide driving force to curve the later-described curving portion 27 of the endoscope 12 in the R-direction and the L-direction in an XZ-plane shown in FIG. 7. The actuator section 21 comprises a motor such as a servomotor.

The endoscope 12 has a universal cord 22, the operation portion 23 which is an example of a grip portion, and an insertion portion 24 to be inserted into a hole (subject). The endoscope 12 is an example of an introduction device.

The endoscope 12 is connected to the control device 13, the light source device 14, the image taking device 15, and the air/water/suction device 16 via the universal cord 22. A flexible shaft (not shown) is passed through the universal cord 22. The driving force of the actuator section 21 is transmitted to a pair of second wires 32 (see FIG. 3 and FIG. 4) for curving the curving portion 27 wound around a pulley (second pulley) in the R-direction and the L-direction via, for example, the flexible shaft and a gear and the pulley provided inside the operation portion 23.

Figure 3:
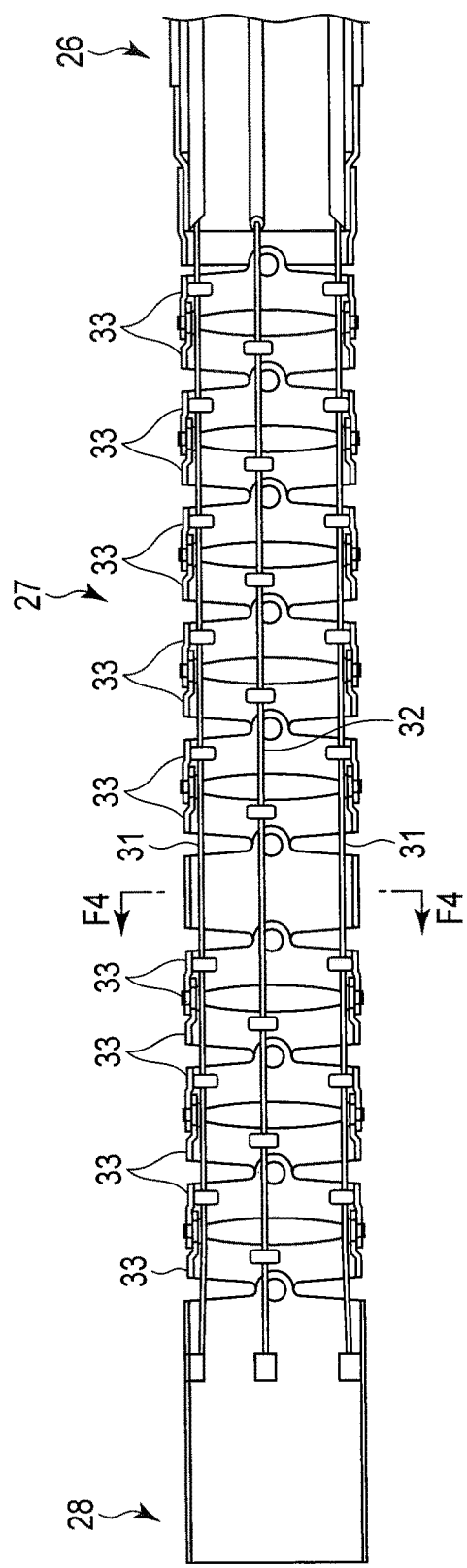
FIG. 3 is a sectional view showing curving pieces and wires inside a curving portion of the endoscopic apparatus shown in FIG. 1.
Figure 6:
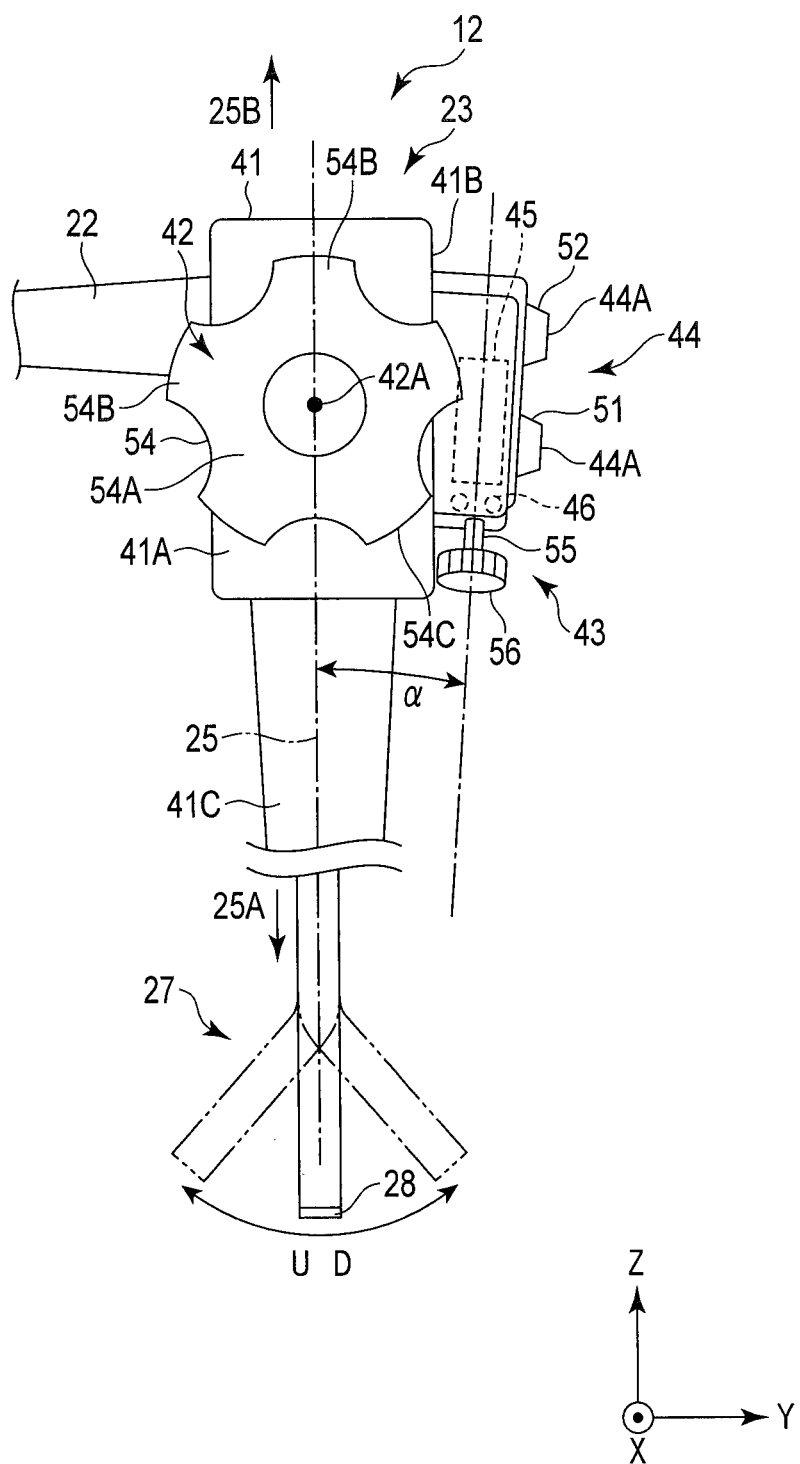
FIG. 6 is a schematic diagram showing the operation portion of the endoscopic apparatus shown in FIG. 5 from a direction D1 in which a first wall portion is seen.

The insertion portion 24 is provided along a longitudinal axis 25 of the operation portion 23 (see FIG. 6 and others). The longitudinal axis 25 is parallel to a Z-axis. In FIG. 6 and others, an arrow 25A indicates the distal direction of the longitudinal axis 25, and an arrow 25B indicates the proximal direction of the longitudinal axis 25. The insertion portion 24 comprises an elongated and flexible soft portion 26, the curving portion 27 provided at the distal end of the soft portion 26, and the distal hard portion 28 provided at the distal end of the curving portion 27. As shown in FIG. 3 and FIG. 4, a pair of first wires 31 for curving the curving portion 27 in the U-direction and the D-direction, a pair of second wires 32 for curving the curving portion 27 in the R-direction and the L-direction are inserted through the soft portion 26 and the curving portion 27. The curving portion 27 has curving pieces 33 arranged in the longitudinal direction of the insertion portion 24.

As shown in FIG. 2, the distal hard portion 28 is provided with the objective lens 34, a treatment instrument insertion channel 35, the illumination lens 36, and the nozzle 37 capable of supplying water and air to clean the distal end face of the distal hard portion 28 and sucking, for example, liquid or tissues in a living body.

As shown in FIG. 5 and FIG. 6, the operation portion 23 has a case 41 formed to have an internal space by, for example, a synthetic resin material, a first dial unit (first curving operation unit) 42 provided in a first wall portion 41A of the case 41, a second dial unit (second curving operation unit) 43 provided in a second wall portion 41B of the case 41, a button section 44 provided in the second wall portion 41B of the case 41, the rotation detection sensor 45 provided inside the case 41, and an O-ring 46 provided around a second shaft 55 of the second dial unit 43. Each of the first wall portion 41A and the second wall portion 41B may be a flat surface or a curved surface. When the first wall portion 41A and the second wall portion 41B are curved surfaces, the first wall portion 41A and the second wall portion 41B are preferably formed to project outward relative to the longitudinal axis.

The case 41 has a support portion 41C which is located closer to the curving portion 27 than the first wall portion 41A and the second wall portion 41B when a doctor holds the operation portion 23 with the left hand and which is supported by the third finger and the little finger of the left hand. When the operation portion 23 is held with the left hand, the tip of the third finger and the tip of the little finger are located closer to the wrist than the tip of the first finger and the tip of the second finger so that the hand is not easily strained. Thus, the parts of the support portion 41C supported by the third finger and the little finger are preferably formed so that their length around the longitudinal axis 25 is smaller than that of the parts formed by the first wall portion 41A and the second wall portion 41B of the case 41.

The first wall portion 41A extends in the direction along a later-described first dial portion 54 of the first dial unit 42 (or the radial direction of a first shaft 53 of the first dial unit 42). The second wall portion 41B is adjacent to the first wall portion 41A. Specifically, the second wall portion 41B extends from the outer edge of the first wall portion 41A in a direction which intersects (at right angles) with the first wall portion 41A. In other words, the second wall portion 41B extends from the outer edge of the first wall portion 41A along the direction in which the later-described first shaft 53 of the first dial unit 42 extends. The O-ring 46 intervenes between the second shaft 55 and the case 41, and water-tightly maintains the inside of the case 41. The O-ring 46 gives predetermined rotational resistance (resistance force) to the second shaft 55.

The rotation detection sensor 45 comprises, for example, a potentiometer, but may be any other kind of sensor (e.g. a rotary encoder) that can detect the rotation amount of the second shaft 55. The rotation detection sensor 45 reads the rotation angle of the second dial portion 56 via the second shaft 55 of the second dial unit 43 to detect the rotation direction and rotation amount of the second dial portion 56.

Figure 7:
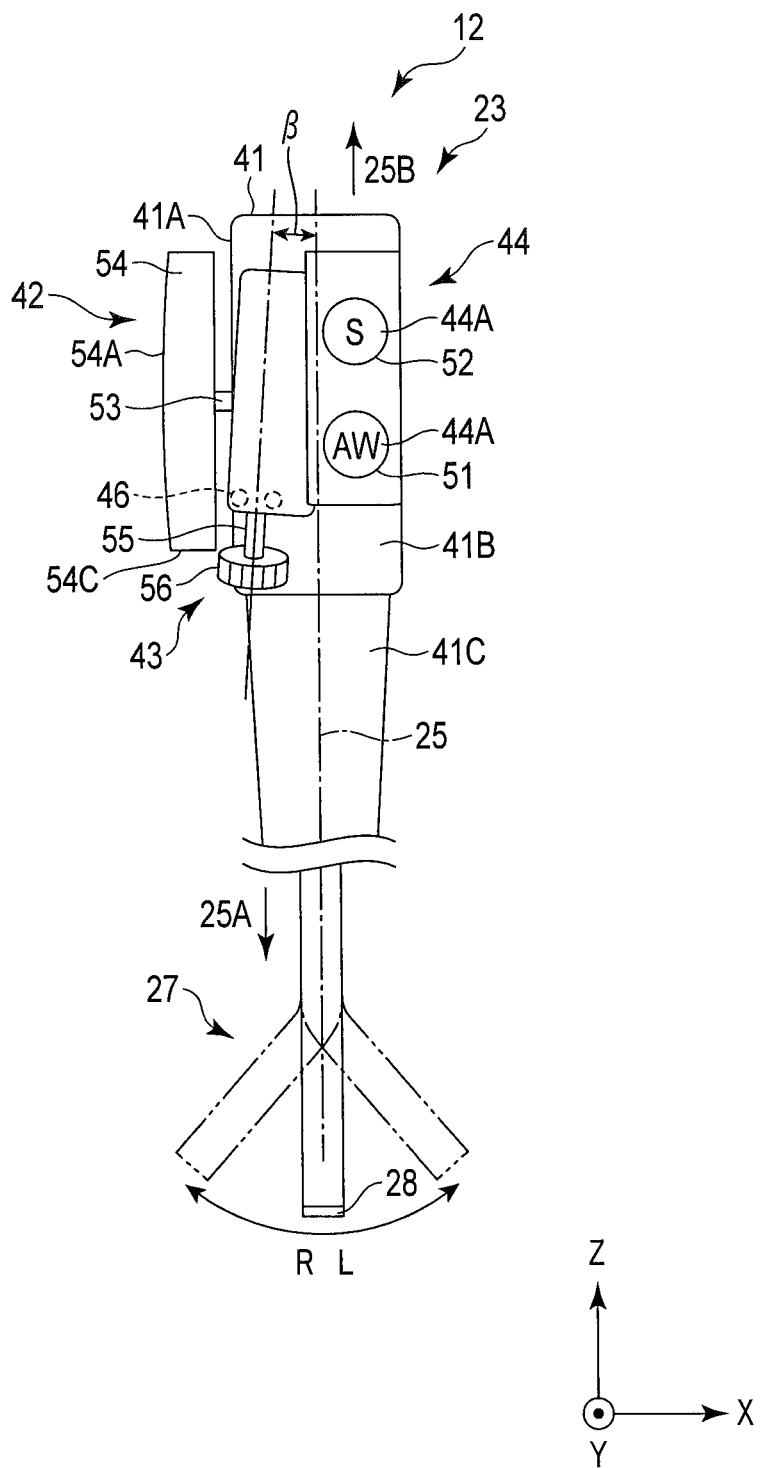
FIG. 7 is a schematic diagram showing the operation portion of the endoscopic apparatus shown in FIG. 5 from a direction D2 in which a second wall portion is seen.

As shown in FIG. 6 and FIG. 7, the button section 44 has a first button 51 (air/water supply button, AW) to supply air/water to the distal hard portion 28 of the endoscope 12 via the nozzle 37, and a second button 52 (suction button, S) for sucking by the distal hard portion 28 of the endoscope 12 via the nozzle 37. The first button 51 and the second button 52 each have a top surface (a second top surface 44A).

The first dial unit 42 is what is known as a UD angle knob which is operated to curve the curving portion 27 in the U-direction and the D-direction, that is, two directions. If the user rotates the first dial unit 42 around its central axis 42A, the curving portion 27 is curved in the U-direction and the D-direction in a YZ-plane shown in FIG. 6 in accordance with the rotation amount of the first dial unit 42. That is, the endoscopic apparatus 11 according to the present embodiment is not provided with a mechanism which electrically curves the curving portion 27 by, for example, a motor in the U-direction and the D-direction. However, as in the R-direction and the L-direction which will be described later, the actuator section 21, for example, a motor may be provided so that the curving portion 27 is also electrically curved in the U-direction and the D-direction. The YZ-plane is one example of a first surface. The central axis 42A of the first dial unit 42 is preferably formed to intersect, for example, at right angles with the longitudinal axis 25.

As shown in FIG. 5 and FIG. 6, the first dial unit 42 has the first shaft 53 rotatably provided in the first wall portion 41A, the first dial portion (first knob) 54 fixed to one end of the first shaft 53, and a first pulley (not shown) which is provided inside the case 41 and which is fixed to the other end of the first shaft 53. The first dial portion 54 includes a first top surface 54A. The first dial portion 54 is substantially star-shaped, and has, for example, five claws 54B. The first wires 31 to curve the curving portion 27 in the U-direction and the D-direction are wound around the first pulley.

The second dial unit 43 (dial unit) is what is known as an RL angle knob which is operated to curve the curving portion 27 in the R-direction and the L-direction, that is, two directions. If the user rotates the second dial unit 43, the actuator section 21 is driven in accordance with the rotation amount of the second dial unit 43. The curving portion 27 is electrically curved in the R-direction and the L-direction in the XZ-plane shown in FIG. 7 by the driving force of the actuator section 21 in accordance with the rotation amount of the second dial unit 43. The XZ-plane is one example of a second surface, and intersects at right angles with the above-mentioned YZ-plane (see FIG. 6). Although the curving portion 27 is electrically curved in the R-direction and the L-direction in the example described according to the present embodiment, the curving portion 27 may also be manually curved in the R-direction and the L-direction as in the case of the curving mechanism which curves the curving portion 27 in the U-direction and the D-direction.

The second dial unit 43 has the second shaft 55 which is provided on the side of the second wall portion 41B and which is rotatable relative to the case 41, and the second dial portion (second knob) 56 fixed to one end of the second shaft 55. The second dial portion 56 has a circular cylindrical shape. The circumferential surface of the second dial portion 56 is, for example, knurled. The second dial portion 56 is provided closer to the curving portion 27 than the central axis 42A of the first dial portion 54 in the direction of the longitudinal axis 25. The other end of the second shaft 55 is connected to the rotation detection sensor 45 inside the case 41.

The second shaft 55 is one example of a shaft in the present invention. As shown in FIG. 6, the second shaft 55 is disposed obliquely to the longitudinal axis 25 of the operation portion 23 when seen from a direction D1 (the side of the first wall portion 41A) in which the first wall portion 41A (the first top surface 54A) is seen (see FIG. 5). More specifically, the second shaft 55 is obliquely disposed in a direction to approach the longitudinal axis 25 as the second shaft 55 goes further in the distal direction 25A of the longitudinal axis 25 when seen from the direction D1 (the side of the first wall portion 41A) in which the first wall portion 41A (the first top surface 54A) is seen. In other words, the second shaft 55 is obliquely disposed in a direction to approach the longitudinal axis 25 as the second shaft 55 goes further in the distal direction 25A of the longitudinal axis 25 when seen from a direction which is parallel to the first shaft 53 and which is perpendicular to the longitudinal axis 25. The second shaft 55 is inclined at an angle α with the longitudinal axis 25 when seen from the direction D1 (the side of the first wall portion 41A) in which the first wall portion 41A is seen. In this instance, the angle α is set to a proper angle, for example, in the range of 5° to 15°.

Figure 8:
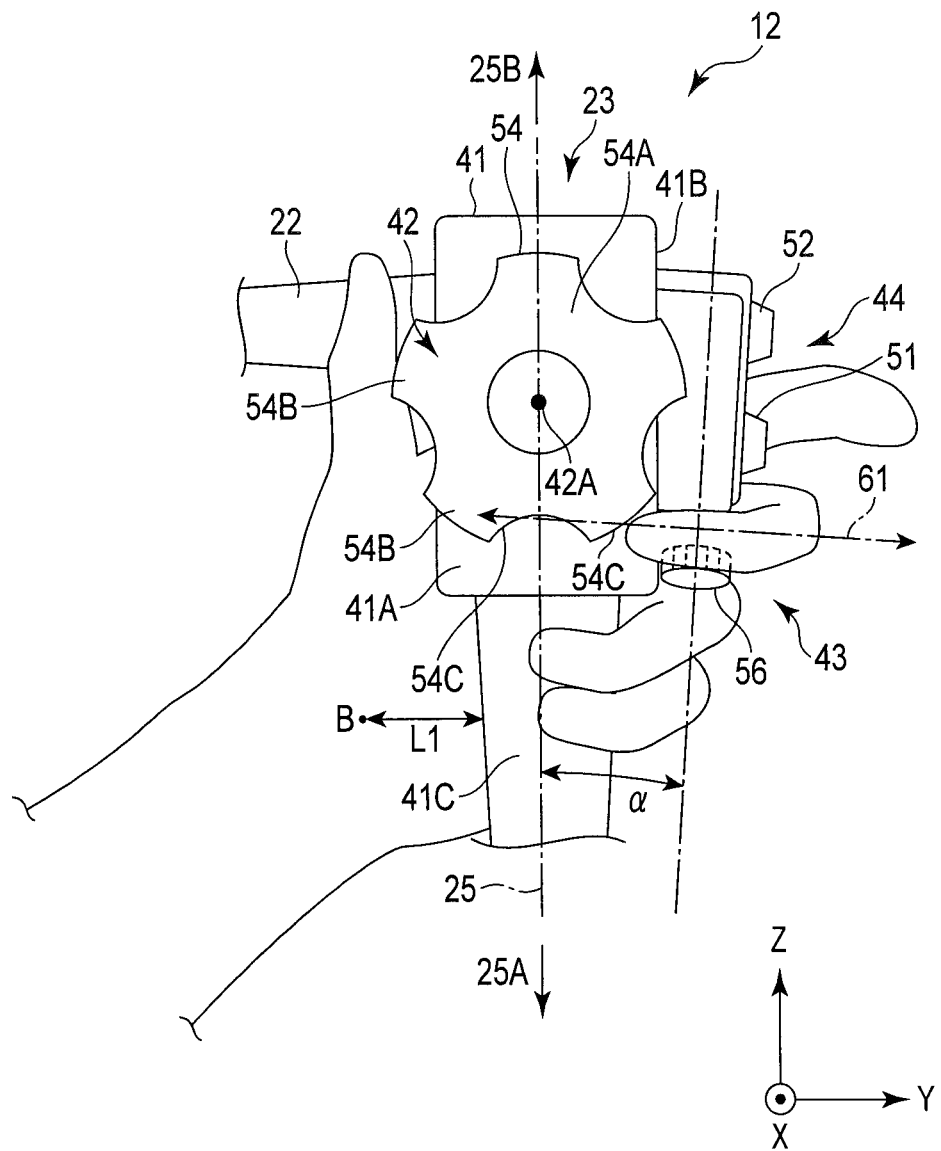
FIG. 8 is a schematic diagram showing how the operation portion of the endoscopic apparatus shown in FIG. 6 is grasped with the left hand.

How the user grasps the operation portion 23 is shown in FIG. 8. As shown in FIG. 8, when seen from the direction D1 (the side of the first wall portion 41A) in which the first wall portion 41A is seen, an operation axis line 61 of the finger which rotates the second dial portion 56 is tangent to a lower edge 54C of the first dial portion 54 (located at the end of the distal direction 25A in the direction of the longitudinal axis 25). That is, the second dial portion 56 is provided in such a positional relation to the first dial portion 54. The operation axis line 61 of the finger substantially intersects at right angles with the direction in which the second shaft 55 extends.

As shown in FIG. 7, the second shaft 55 is disposed obliquely to the longitudinal axis 25 of the operation portion 23 when seen from a direction D2 (the side of the second wall portion 41B) in which the second wall portion 41B (the second top surface 44A) is seen in front (see FIG. 5). More specifically, the second shaft 55 is obliquely disposed in a direction to depart from the longitudinal axis 25 as the second shaft 55 goes further in the distal direction 25A of the longitudinal axis 25 when seen from the direction D2 (the side of the second wall portion 41B) in which the second wall portion 41B is seen. That is, the second shaft 55 is obliquely disposed in a direction to approach the first wall portion 41A (or the first dial portion 54) as the second shaft 55 goes further in the distal direction 25A of the longitudinal axis 25 when seen from the direction D2 (the side of the second wall portion 41B) in which the second wall portion 41B is seen. The second shaft 55 is obliquely disposed in a direction to depart from the longitudinal axis 25 as the second shaft 55 goes further in the distal direction 25A of the longitudinal axis 25 when seen from a direction which is perpendicular to the first shaft 53 (the central axis 42A) and perpendicular to the longitudinal axis 25 and in which the fingers of the user other than the thumb are located. The second shaft 55 is inclined at an angle β with the longitudinal axis 25 when seen from the direction D2 (the side of the second wall portion 41B) in which the second wall portion 41B is seen. In this instance, the angle β is set to a proper angle, for example, in the range of 5° to 15°.

Figure 9:
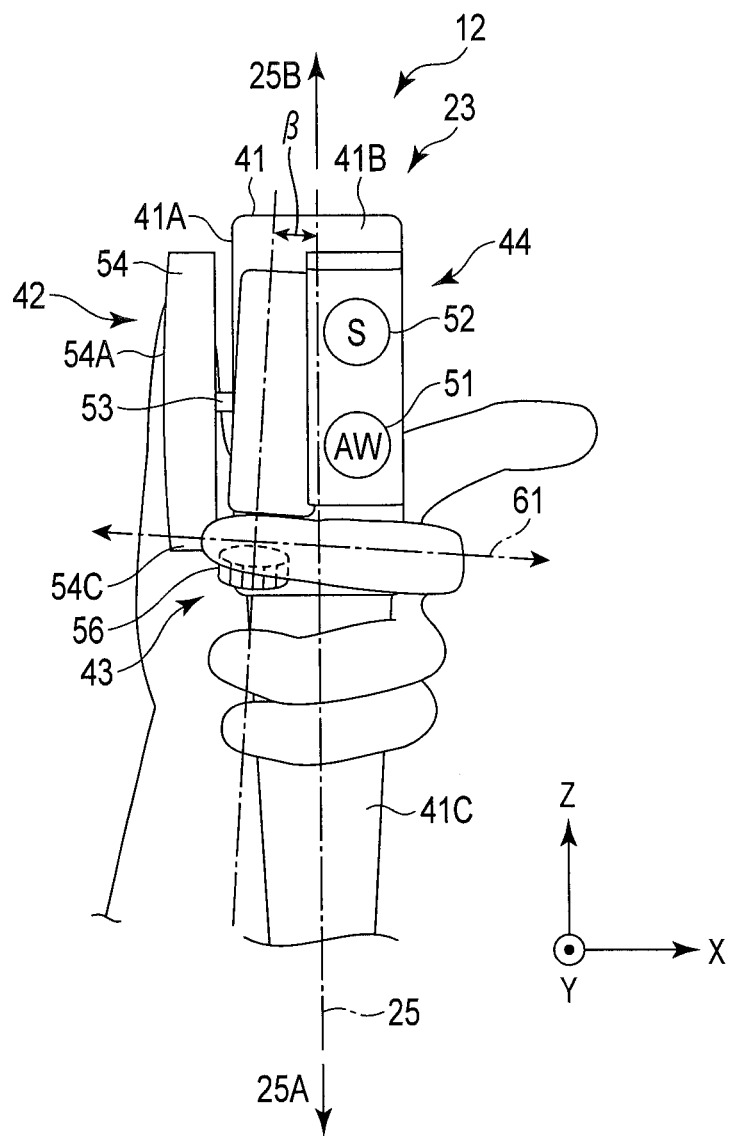
FIG. 9 is a schematic diagram showing how the operation portion of the endoscopic apparatus shown in FIG. 7 is grasped with the left hand.

How the user grasps the operation portion 23 is shown in FIG. 9. As shown in FIG. 9, when seen from the direction D2 in which the second wall portion 41B is seen, the operation axis line 61 of the finger which rotates the second dial portion 56 is tangent to the lower edge 54C of the first dial portion 54 (located at the end of the distal direction 25A in the direction of the longitudinal axis 25). That is, the second dial portion 56 is provided in such a positional relation to the first dial portion 54. The operation axis line 61 of the finger substantially intersects at right angles with the direction in which the second shaft 55 extends.

That is, the second shaft 55 and the second dial portion 56 are inclined relative to the longitudinal axis 25 of the operation portion 23 according to this embodiment when seen from both the direction D1 (the side of the first wall portion 41A) and the direction D2 (the side of the second wall portion 41B) in FIG. 5. Thus, the second shaft 55 and the second dial portion 56 are three-dimensionally inclined relative to the longitudinal axis 25 of the operation portion 23.

The outside diameter of the second dial portion 56 is properly set in relation to the first dial portion 54. As shown in FIG. 7, when the second dial portion 56 is seen from the direction D2 in which the second wall portion 41B is seen in front, the position of the second dial portion 56 which is distal to the longitudinal axis 25 is located closer to the longitudinal axis 25 than the first top surface 54A of the first dial portion 54 which is distal to the longitudinal axis 25 in the X-axis direction. As shown in FIG. 6, when the second dial portion 56 is seen from the direction D1 in which the first wall portion 41A is seen in front, the position of the second dial portion 56 which is distal to the longitudinal axis 25 is located farther from the longitudinal axis 25 than the part of the first dial portion 54 which is distal to the longitudinal axis 25 in the Y-axis direction.

Now, the operation of the endoscopic apparatus 11 according to the present embodiment is described.

The doctor who is the user grasps the operation portion 23, for example, with the left hand. The doctor puts the universal cord 22 at a position between the thumb and the first finger of the left hand, locates the ball of the thumb on the claw 54B of the first dial portion 54, and supports the support portion 41C with the third finger and the little finger. The doctor then locates the ball of the first finger of the left hand at a position to be able to operate the first button (air/water button) 51 and the second button (suction button) 52, and locates the ball of the second finger on the second dial portion 56. Thus, the doctor turns the left hand in the X-direction from the Y-direction to hold the operation portion 23 therearound, and then holds the insertion portion 24 with the right hand and inserts the insertion portion 24 into the hole, and can then conduct a desired inspection or treatment.

When the doctor desires to curve the curving portion 27 in one of the U-direction and the D-direction in the YZ-plane, the doctor rotates the first dial portion 54 with, for example, the ball of the thumb of the left hand clockwise or counterclockwise, as shown in FIG. 8. As a result, the first pulley fixed to the first shaft 53 inside the operation portion 23 rotates, and one of a pair of first wires 31 wound around the first pulley is pulled toward the proximal end of the operation portion 23 so that the curving portion 27 curves in one of the U-direction and the D-direction. Specifically, the curving portion 27 curves in the D- (downward) direction if the first dial portion 54 in FIG. 6 and FIG. 8 is rotated clockwise, whereas the curving portion 27 curves in the U- (upward) direction if the first dial portion 54 is rotated counterclockwise.

In this instance, for example, when the doctor desires to rotate the first dial portion 54 by one of the claws 54B (about 72 degrees) and then further rotate the first dial portion 54 by one of the claws 54B (about 72 degrees) in the same direction, the doctor uses the second finger of the left hand together with the thumb of the left hand as shown in FIG. 8 to prevent the curving angle of the curving portion 27 from decreasing because the tension of the pulled first wires 31 can not be maintained. After having rotated the first dial portion 54 by one of the claws 54B (about 72 degrees), the doctor temporarily holds, that is, assists the first dial portion 54 with the tip of the second finger of the left hand to stop the rotation of the first dial portion 54.

In this instance, as shown in FIG. 8, the second shaft 55 and the second dial portion 56 are inclined relative to the longitudinal axis 25, and the operation axis line 61 of the finger which rotates the second dial portion 56 is located at the position which is tangent to the edge 54C of the first dial portion 54. Thus, the distance between the second dial portion 56 and the claw 54B of the first dial portion 54 is smaller than when the second shaft 55 and the second dial portion 56 are parallel to the longitudinal axis 25.

As shown in FIG. 9, the second shaft 55 and the second dial portion 56 are inclined relative to the longitudinal axis 25, and the operation axis line 61 of the finger which rotates the second dial portion 56 is located at the position which is tangent to the lower edge 54C of the first dial portion 54. Therefore, the longitudinal axis 25 of the operation portion 23 is disposed to be three-dimensionally inclined relative to the second shaft 55 and the second dial portion 56. Thus, when the left hand of a doctor who operates the operation portion 23 of the endoscope 12 is relatively large and the second finger is long, the doctor locates the ball of the second finger on the second dial portion 56, and holds the claw 54B close to the second dial portion 56 or the part between the claw 54B close to the second dial portion 56 and the distal claw 54B on the operation axis line 61. When the left hand is relatively small and the second finger is short, the doctor locates the ball of the second finger on the second dial portion 56 to hold the second dial portion 56, and holds the claw 54B close to the second dial portion 56.

Thus, when holding, that is, assisting the claw 54B of the first dial portion 54 while holding the second dial portion 56 with the ball of the second finger of the left hand, the doctor does not need to force the second finger of the left hand to extend or bend even if the tip of the second finger of the left is put on the lower part of the first dial portion 54. Thus, when operating the second dial portion 56 and also assisting the first dial portion 54, the doctor does not need to force the finger to extend or bend, and it is possible to maximally prevent the doctor from being fatigued.

As shown in FIG. 9, the position of the second dial portion 56 which is distal to the longitudinal axis 25 is located closer to the longitudinal axis 25 than the first top surface 54A of the first dial portion 54 which is distal to the longitudinal axis 25. Thus, when supporting the claw 54B of the first dial portion 54 while holding the second dial portion 56 with, for example, the second finger, the doctor does not need to perform any operation in which, for example, the distal interphalangeal joint of the second finger is forced to bend, so that the strain on the doctor can be reduced.

Therefore, if the endoscope 12 according to this embodiment is used, even a doctor with relatively small hands can operate the second dial portion 56 with the second finger of the left hand and also easily assist the first dial portion 54 with the same second finger of the left hand. Thus, even a doctor with relatively small hands does not need take the right had off the insertion portion 24 to hold the first dial portion 54, and can maintain the curving state of the curving portion 27 in the U-direction and the D-direction while, for example, holding the insertion portion 24 twisted. In this instance, if the second dial portion 56 is held while the first dial portion 54 is held with the second finger of the left hand, it is possible to not only hold the curving state of the curving portion 27 in the U-direction and the D-direction but also hold the curving state of the curving portion 27 in the R-direction and the L-direction. That is, even a doctor with relatively small hands can curve the curving portion 27 in the U-direction, the D-direction, the R-direction, and the L-direction with one hand.

Thus, in the assist state to hold the first dial portion 54 with the second finger of the left hand, the thumb of the left hand is taken off the first dial portion 54 and then moved to the adjacent claw 54B to hold the first dial portion 54. After taking the second finger of the left hand off the first dial portion 54, the doctor can further rotate the first dial portion 54 by one of the claws 54B (about 72 degrees) in the same direction.

In contrast, when the doctor desires to curve the curving portion 27 in one of the R-direction and the L-direction in the XZ-plane, the doctor rotates the second dial portion 56 with, for example, the ball of the second finger of the left hand clockwise or counterclockwise, as shown in FIG. 8 and FIG. 9. The curving portion 27 curves in the R- (rightward) direction if the second dial portion 56 in FIG. 5 is rotated clockwise, whereas the curving portion 27 curves in the L- (leftward) direction if the second dial portion 56 is rotated counterclockwise.

In this instance, as shown in FIG. 8, when seen from the direction D1 in which the first wall portion 41A is seen in front (see FIG. 5), the operation axis line 61 of the finger which rotates the second dial portion 56 is tangent to the lower edge 54C of the first dial portion 54. As shown in FIG. 9, when seen from the direction D2 in which the second wall portion 41B is seen in front (see FIG. 5), the operation axis line 61 of the finger which rotates the second dial portion 56 is tangent to the lower edge 54C of the first dial portion 54. That is, a movement surface in which the second finger of the left hand moves is slightly inclined relative to an XY-plane, and does not intersect at right angles with the XZ-plane in which the curving portion 27 curves in the R-direction and the L-direction. According to these structures, the user can smoothly perform the above-mentioned assist operation for the first dial portion 54 with the finger (second finger) which operates the second dial portion 56.

The rotation amount of the second dial portion 56 is read by the rotation detection sensor 45. The rotation detection sensor 45 does not hinder the rotation of the second dial portion 56, and no great force is required for the rotation of the second dial portion 56.

The rotation detection sensor 45 transmits an electric signal corresponding to the rotation amount of the second dial portion 56 to the control device 13. The control device 13 actuates the actuator section 21 so that the actuator section 21 transmits torque (rotational force) to a pair of second wires 32 via the flexible shaft, the gear, and the second pulley. Thus, one of the second wires 32 is pulled toward the proximal side of the operation portion 23 so that the curving portion 27 curves in one of the R-direction and the L-direction.

According to the first embodiment, the introduction device comprises a grip portion (case 41) having the first wall portion 41A and the second wall portion 41B extending in a direction that intersects at right angles with the first wall portion 41A, and a dial unit having the curving portion 27 which is provided along the longitudinal axis 25 of the grip portion and which can curve in a first surface and in a second surface that intersects at right angles with the first surface, the first dial portion 54 which is rotatably provided on the side of the first wall portion 41A and which curves the curving portion 27 in the first surface in accordance with the rotation amount, a shaft rotatably provided on the side of the second wall portion 41B, and the second dial portion 56 which is fixed to the shaft and which curves the curving portion 27 in the second surface in accordance with a rotation amount. The second shaft 55 is disposed obliquely to the longitudinal axis 25 when seen from the side of the second wall portion 41B. Although the first surface formed by the U-direction and the D-direction intersects at right angles with the second surface formed by the R-direction and the L-direction in the example described according to this embodiment, the surfaces have only to be different surfaces even if these surfaces do not intersect with each other. This also applies to embodiments which will be described later.

According to this configuration, the shaft 55 of the dial unit can be disposed obliquely to the longitudinal axis 25 when seen from the side of the second wall portion 41B. Consequently, it is possible to provide an introduction device having the easily operable shaft 55 in accordance with the size of the hand of the user. It is therefore possible to eliminate the deterioration of operational feeling caused by the difference of the size of the user's hands.

The shaft 55 is obliquely disposed in a direction to approach the first wall portion 41A as the shaft 55 goes further in the distal direction 25A of the longitudinal axis 25 when seen from the side of the second wall portion 41B. The shaft 55 is obliquely disposed in a direction to approach the longitudinal axis 25 as the shaft 55 goes further in the distal direction 25A of the longitudinal axis 25 when seen from the side of the first wall portion 41A. The second dial portion 56 is located closer to the curving portion 27 than the central axis 42A of the first dial portion 54 in the direction of the longitudinal axis 25.

According to these configurations, the second dial portion 56 can be located close to the first wall portion 41A, that is, the side of the first dial portion 54 when seen from the side of the second wall portion 41B. Moreover, the second dial portion 56 can be located close to the first dial portion 54 when seen from the side of the first wall portion 41A. As a result, even a user with small hands (e.g. a female doctor) can smoothly operate the first dial portion 54 and the second dial portion 56. In particular, the shaft 55 is inclined relative to the longitudinal axis 25, so that the second dial portion 56 can be located close to the first dial portion 54, and even a user with small hands can smoothly perform the operation (assist operation) for temporarily holding the position of the first dial portion 54 with the finger (second finger) which operates the second dial portion 56. Consequently, it is possible to further improve the operational feeling of the introduction device when curving the curving portion 27 in the U-direction and the D-direction.

The second dial portion 56 is provided so that the operation axis line 61 of the finger which rotates the second dial portion 56 is tangent to the edge 54C of the first dial portion 54 which is located at the end of the distal direction 25A in the direction of the longitudinal axis 25, when seen from the side of the second wall portion 41B. Moreover, the second dial portion 56 is provided so that the operation axis line 61 of the finger which rotates the second dial portion 56 is tangent to the edge 54C of the first dial portion 54 which is located at the end of the distal direction 25A in the direction of the longitudinal axis 25, when seen from the side of the first wall portion 41A. According to these configurations as well, the assist operation for the first dial portion 54 can be more easily performed with the finger which operates the second dial portion 56. Consequently, it is possible to improve the operational feeling of the introduction device.

The side of the second dial portion 56 closer to the curving portion 27 is closer to the longitudinal axis 25 when the operation portion 23 of the endoscope 12 according to this embodiment is held with the left hand. Therefore, a distance L1 (see FIG. 8) between the support portion 41C and the base of the thumb (or the wrist) B can be greater than a distance L2 (see FIG. 12) between the support portion 41C and the base of the thumb (or the wrist) B according to the second embodiment which will be described later. Thus, the endoscope 12 according to this embodiment allows the distance (gap) between the support portion 41C and the base of the thumb (or the wrist) B to be relatively great, allows a higher degree of freedom in moving the wrist, allows a doctor with relatively small hands to easily hold the operation portion 23, and allows the first dial portion 54 and the second dial portion 56 to be properly operated.

For example, a recess (not shown) to locate the second finger is preferably formed in the part of the case 41 of the operation portion 23 between the shaft 55 and the first button 51. The recess allows a short second finger of a doctor with a small left hand to be easily disposed on the edge 54C of the first dial portion 54.

Although the second dial portion 56 drawn in FIG. 6 is located on the outer side of the case 41, the case 41 may be formed so that the part of the second dial portion 56 close to the longitudinal axis 25 is buried in the first and second wall portions 41A and 41B.

In the example described according to this embodiment, the endoscope 12 is used as an example of the introduction device. Another example that may be used as the introduction device has neither an illumination optical system including the light source device 14, the illumination lens 36 of the distal hard portion 28, and others nor an observation optical system including the image taking device 15, the monitor 18, the objective lens 34 of the distal hard portion 28, and others.

[Second Embodiment]

The endoscopic apparatus 11 according to the second embodiment is described with reference to FIG. 10 to FIG. 13. Although the endoscopic apparatus 11 according to the second embodiment is different from that according to the first embodiment in the angle at which the second dial unit 43 is provided, but is the same as that according to the first embodiment in other respects. Therefore, the differences between the first embodiment and the second embodiment are mainly described, and the same parts are neither shown nor described.

Figure 10:
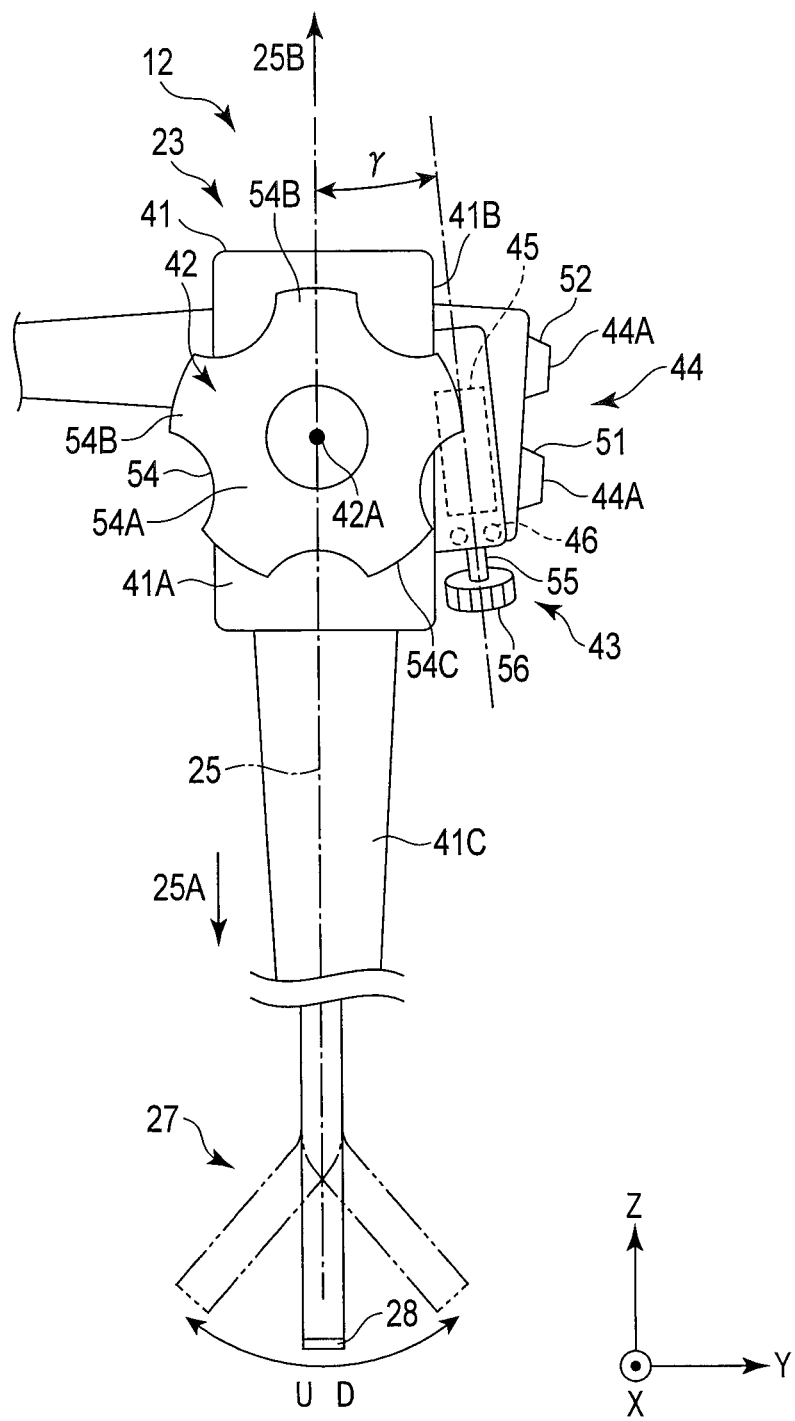
FIG. 10 is a schematic diagram showing the operation portion of the endoscopic apparatus according to a second embodiment from the direction D1 in which the first wall portion is seen.

As shown in FIG. 10 and FIG. 11, the second dial unit 43 is what is known as an RL angle knob. If the user rotates the second dial unit 43, the actuator section 21 is driven in accordance with the rotation amount of the second dial unit 43. The curving portion 27 is electrically curved in the R-direction and the L-direction in the XZ-plane by the driving force of the actuator section 21. The XZ-plane is one example of a second surface, and intersects at right angles with the above-mentioned YZ-plane (the U-direction and the D-direction). Although the curving portion 27 is electrically curved in the R-direction and the L-direction in the present embodiment, the curving portion 27 may also be manually curved in the R-direction and the L-direction as in the case of the curving mechanism for the U-direction and the D-direction.

The second dial unit 43 has the second shaft 55 which is provided rotatably relative to the case 41, and the second dial portion 56 fixed to one end of the second shaft 55. The second dial portion 56 has a circular cylindrical shape. The circumferential surface of the second dial portion 56 is, for example, knurled. The second dial portion 56 is provided closer to the curving portion 27 than the first dial portion 54 in the direction of the longitudinal axis 25. The rotation detection sensor 45 is connected to the other end of the second shaft 55.

The second shaft 55 is one example of a shaft. As shown in FIG. 10, the second shaft 55 is disposed obliquely to the longitudinal axis 25 of the operation portion 23 when seen from the direction D1 (the side of the first wall portion 41A) in which the first wall portion 41A (the first top surface 54A) is seen. More specifically, the second shaft 55 is obliquely disposed in a direction to depart from the longitudinal axis 25 as the second shaft 55 goes further in the distal direction 25A of the longitudinal axis 25 when seen from the direction D1 (the side of the first wall portion 41A) in which the first wall portion 41A (the first top surface 54A) is seen. In other words, the second shaft 55 is obliquely disposed in a direction to depart from the longitudinal axis 25 as the second shaft 55 goes further in the distal direction 25A of the longitudinal axis 25 when seen from a direction which is parallel to the first shaft 53 and which is perpendicular to the longitudinal axis 25. The second shaft 55 is inclined at an angle γ with the longitudinal axis 25 when seen from the direction D1 (the side of the first wall portion 41A) in which the first wall portion 41A is seen. In this instance, the angle γ is set to a proper angle, for example, in the range of 5° to 15°.

Figure 12:
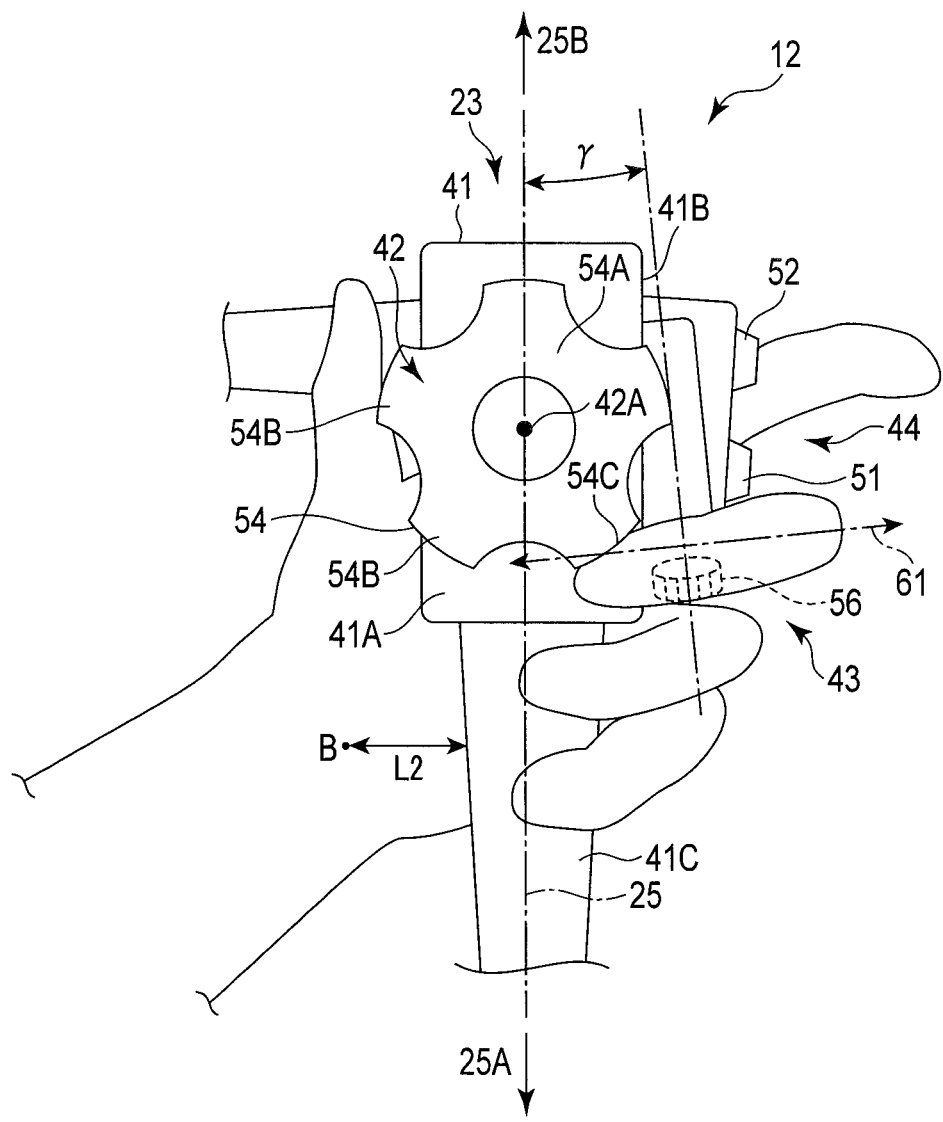
FIG. 12 is a schematic diagram showing how the operation portion of the endoscopic apparatus shown in FIG. 10 is grasped with the left hand.

How the user grasps the operation portion 23 is shown in FIG. 12. As shown in FIG. 12, when seen from the direction D1 (the side of the first wall portion 41A) in which the first wall portion 41A is seen, the operation axis line 61 of the finger which rotates the second dial portion 56 is tangent to the edge 54C of the first dial portion 54 located at the end of the distal direction 25A in the direction of the longitudinal axis 25. That is, the second dial portion 56 is provided in such a positional relation to the first dial portion 54. The operation axis line 61 of the finger (second finger) substantially intersects at right angles with the direction in which the second shaft 55 extends.

As shown in FIG. 11, the second shaft 55 is disposed obliquely to the longitudinal axis 25 of the operation portion 23 when seen from the direction D2 (the side of the second wall portion 41B) in which the second wall portion 41B (the second top surface 44A) is seen. More specifically, the second shaft 55 is obliquely disposed in a direction to approach the longitudinal axis 25 as the second shaft 55 goes further in the distal direction 25A of the longitudinal axis 25 when seen from the direction D2 (the side of the second wall portion 41B) in which the second wall portion 41B is seen. That is, the second shaft 55 is obliquely disposed in a direction to depart from the first wall portion 41A (or the first dial portion 54) as the second shaft 55 goes further in the distal direction 25A of the longitudinal axis 25 when seen from the direction D2 (the side of the second wall portion 41B) in which the second wall portion 41B is seen. The second shaft 55 is obliquely disposed in a direction to depart from the longitudinal axis 25 as the second shaft 55 goes further in the distal direction 25A of the longitudinal axis 25 when seen from a direction which is perpendicular to the first shaft 53 (the central axis (42A)) and perpendicular to the longitudinal axis 25 and in which the fingers of the user other than the thumb are located. The second shaft 55 is inclined at an angle δ with the longitudinal axis 25 when seen from the direction D2 (the side of the second wall portion 41B) in which the second wall portion 41B is seen. In this instance, the angle δ is set to a proper angle, for example, in the range of 5° to 15°.

Figure 13:
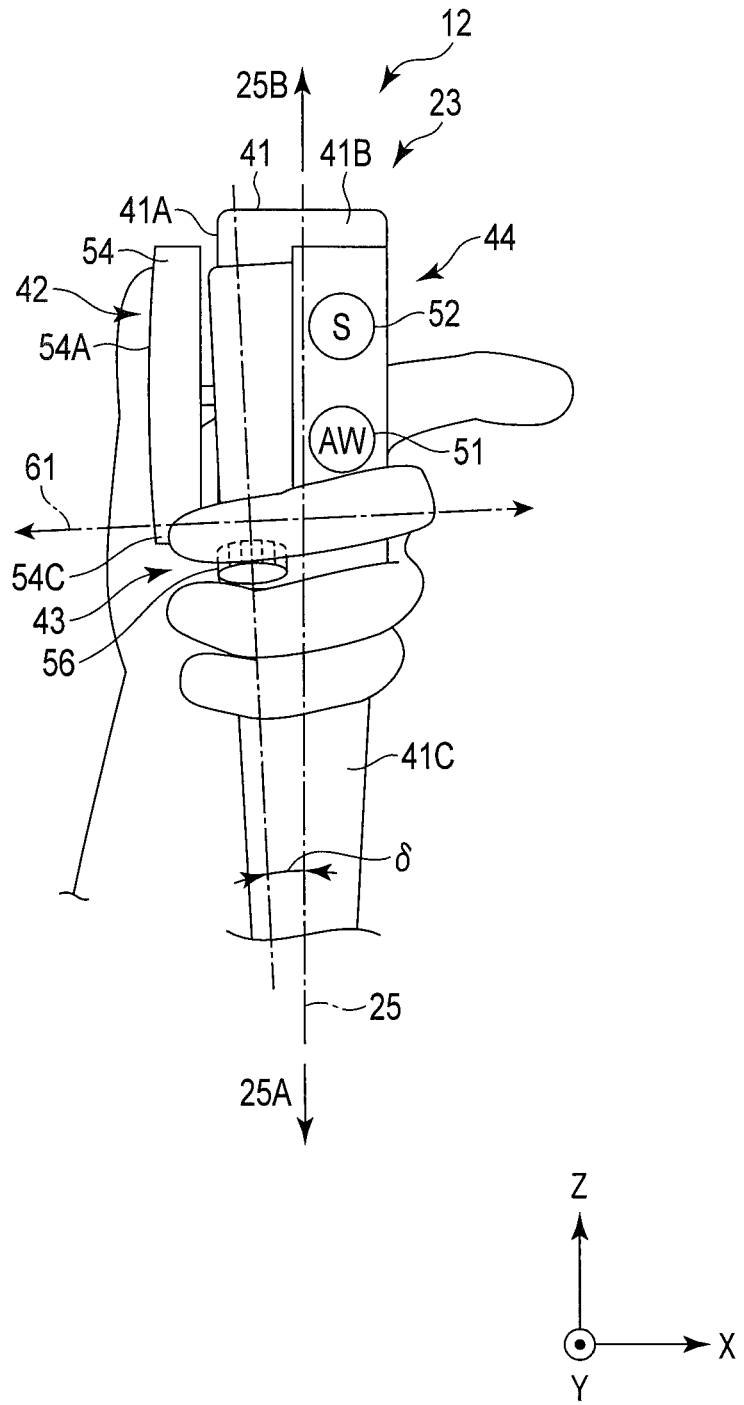
FIG. 13 is a schematic diagram showing how the operation portion of the endoscopic apparatus shown in FIG. 11 is grasped with the left hand.

How the user grasps the operation portion 23 is shown in FIG. 13. In this instance, as shown in FIG. 13, when seen from the direction D2 (the side of the second wall portion 41B) in which the second wall portion 41B is seen, the operation axis line 61 of the finger which rotates the second dial portion 56 is tangent to the lower edge 54C of the first dial portion 54 located at the end of the distal direction 25A in the direction of the longitudinal axis 25. That is, the second dial portion 56 is provided in such a positional relation to the first dial portion 54. The operation axis line 61 of the finger (second finger) substantially intersects at right angles with the direction in which the second shaft 55 extends.

Now, the operation of the endoscopic apparatus 11 according to the second embodiment is described.

The doctor who is the user inserts the insertion portion 24 into the hole with the right hand while grasping the operation portion 23, for example, with the left hand, and can then conduct a desired inspection or treatment. When the doctor desires to curve the curving portion 27 in one of the U-direction and the D-direction in the YZ-plane, the doctor rotates the first dial portion 54 with, for example, the ball of the thumb of the left hand clockwise or counterclockwise, as shown in FIG. 12. As a result, the first pulley provided at the other end of the first shaft 53 rotates, and one of a pair of first wires 31 wound around the first pulley is pulled toward the proximal end of the operation portion 23 so that the curving portion 27 curves in one of the U-direction and the D-direction.

In this instance, for example, when the doctor desires to rotate the first dial portion 54 by one of the claws 54B (about 72 degrees) and then further rotate the first dial portion 54 by one of the claws 54B (about 72 degrees) in the same direction, the doctor uses the second finger of the left hand as shown in FIG. 12. After having rotated the first dial portion 54 by one of the claws 54B (about 72 degrees), the doctor temporarily holds, that is, assists the first dial portion 54 with the tip of the second finger of the left hand to stop the rotation of the first dial portion 54.

Thus, in the assist state to hold the first dial portion 54 with the second finger of the left hand, the thumb of the left hand is taken off the first dial portion 54 and then moved to the adjacent claw 54B to hold the first dial portion 54. After taking the thumb of the left hand off the first dial portion 54, the doctor can further rotate the first dial portion 54 by one of the claws 54B (about 72 degrees) in the same direction.

In contrast, when the doctor desires to curve the curving portion 27 in one of the R-direction and the L-direction in the XZ-plane, the doctor rotates the second dial portion 56 with, for example, the ball of the thumb of the left hand clockwise or counterclockwise, as shown in FIG. 12 and FIG. 13. At this moment, as shown in FIG. 12, when seen from the direction D1 (the side of the first wall portion 41A) in which the first wall portion 41A is seen, the operation axis line 61 of the finger which rotates the second dial portion 56 is tangent to the lower edge 54C of the first dial portion 54. As shown in FIG. 13, when seen from the direction D2 (the side of the second wall portion 41B) in which the second wall portion 41B is seen in front, the operation axis line 61 of the finger which rotates the second dial portion 56 is tangent to the lower edge 54C of the first dial portion 54. That is, the movement surface in which the second finger of the left hand moves is slightly inclined relative to the XY-plane, and does not intersect at right angles with the XZ-plane in which the curving portion 27 curves in the R-direction and the L-direction. According to these structures, the user can smoothly perform the above-mentioned assist operation for the first dial portion 54 with the finger (second finger) which operates the second dial portion 56.

The rotation amount of the second dial portion 56 is read by the rotation detection sensor 45. The rotation detection sensor 45 transmits an electric signal corresponding to the rotation amount of the second dial portion 56 to the control device 13. The control device 13 actuates the actuator section 21 so that the actuator section 21 transmits torque (rotational force) to a pair of second wires 32 via the flexible shaft, the gear, and the second pulley. Thus, one of the second wires 32 is pulled toward the proximal side of the operation portion 23 so that the curving portion 27 curves in one of the U-direction and the D-direction.

According to the second embodiment, the shaft 55 is obliquely disposed in the direction to depart from the first wall portion 41A as the second shaft 55 goes further in the distal direction 25A of the longitudinal axis 25 when seen from the side of the second wall portion 41B. The second shaft 55 is obliquely disposed in the direction to depart from the longitudinal axis 25 as the longitudinal axis 25 goes further in the distal direction 25A of the longitudinal axis 25 when seen from the side of the first wall portion 41A. The second dial portion 56 is located closer to the distal direction 25A of the longitudinal axis 25 than the central axis 42A of the first dial portion 54 in the direction of the longitudinal axis 25.

According to these configurations, the second dial portion 56 can be located at some distance from the first wall portion 41A, that is, the side of the first dial portion 54 when seen from the direction D2 in which the second wall portion 41B is seen. Moreover, the second dial portion 56 can be located at some distance from the first dial portion 54 when seen from the direction D1 in which the first wall portion 41A is seen. As a result, in the case of a user having average-sized hands or hands larger than the average (e.g. a male doctor), the movement of the finger which rotates the second dial portion 56 is not hindered by the first dial portion 54, so that the user can smoothly operate the second dial portion 56.

The endoscope 12 according to this embodiment is intended for a user having average-sized hands or hands larger than the average. Thus, even in the case of the above-mentioned structure, it is not difficult to assist the rotation detection sensor 45 with the finger which rotates the second dial portion 56. Some space kept between the first dial portion 54 and the second dial portion 56 rather contributes to the improvement of the operational feeling for the user having the average-sized hands or the hands larger than the average.

The second dial portion 56 is provided so that the operation axis line 61 of the finger which rotates the second dial portion 56 is tangent to the edge 54C of the first dial portion 54, when seen from the side of the second wall portion 41B. Moreover, the second dial portion 56 is provided so that the operation axis line 61 of the finger which rotates the second dial portion 56 is tangent to the edge 54C of the first dial portion 54 which is located at the end of the distal direction 25A in the direction of the longitudinal axis 25, when seen from the direction D1 in which the first wall portion 41A is seen. According to these configurations, the assist operation for the first dial portion 54 can be more easily performed with the finger which operates the second dial portion 56. Consequently, it is possible to improve the operational feeling of the introduction device when the curving portion 27 is curved.

The present invention is not limited to the embodiments described above, and suitable modifications can be made without departing from the spirit of the invention. The endoscopes according to the embodiments may be combined to configure one endoscope.

REFERENCE SIGNS LIST

11: endoscopic apparatus, 12: endoscope, 13: control device, 21: actuator section, 23: operation portion, 25: longitudinal axis, 27: curving portion, 41A: first wall portion, 41B: second wall portion, 43: second dial unit, 54: first dial portion, 54C: edge, 55: second shaft, 56: second dial portion, 61: operation axis line, D1: direction in which the first wall portion is seen, D2: direction in which the second wall portion is seen.

The invention claimed is:

1. An introduction device comprising:
a grip portion configured to be gripped by an operator, the grip portion having a first wall portion and a second wall portion, the second wall portion extending in a direction that intersects with the first wall portion:
a bending section which is configured to bend;
a first dial portion provided on the first wall portion operable to rotate by the operator to bend the bending section, the first dial portion being rotatable about a first axis intersecting with the first wall portion; and
a second dial portion fixed to a rotatable shaft and provided in the second wall portion of the grip portion, the second dial portion is operated to rotate by the operator to bend the bending section, the shaft being oblique to a longitudinal axis of the grip portion when viewed from an exterior side of the second wall portion,
wherein the bending section is provided along the longitudinal axis of the grip portion and is arranged in a distal direction of the longitudinal axis, the shaft is oblique in a direction to depart from the plane in which the first dial portion is provided as the shaft goes further in the distal direction of the longitudinal axis when viewed from the exterior side of the second wall portion, and
the shaft is obliquely disposed in a direction to depart from the longitudinal axis as the shaft goes further in the distal direction of the longitudinal axis when viewed from an exterior side of the first wall portion.

2. The introduction device according to claim 1, wherein the second dial portion is located closer to the distal direction of the longitudinal axis than the central axis of the first dial portion in the direction of the longitudinal axis.

3. The introduction device according to claim 1, wherein the bending section is provided along the longitudinal axis of the grip and is arranged in a distal direction of the longitudinal axis, when the second dial portion is viewed from the side of the second wall portion, an operation axis line of a finger which rotates the second dial portion is provided to be tangent to a distal edge of the first dial portion.

4. The introduction device according to claim 3, wherein when the second dial portion is viewed from an exterior side of the first wall portion, the operation axis line of the finger which rotates the second dial portion is provided to be tangent to the distal edge of the first dial portion.

5. The introduction device according to claim 1, wherein the bending section is provided along the longitudinal axis of the grip and is arranged in a distal direction of the longitudinal axis, when the second dial portion is viewed from the second wall portion, and the position of the second dial portion is located closer to the longitudinal axis of the grip than the top surface of the first dial portion.

6. An endoscopic apparatus comprising the introduction device according to claim 1.

7. The endoscopic apparatus according to claim 6, comprising:
an actuator section which provides force to bend the bending section; and
a control section which controls the actuator section in accordance with a rotation amount of the second dial portion.

* * * * *